United States Patent
Barber

[11] 3,938,509
[45] Feb. 17, 1976

[54] HAND SPLINT

[76] Inventor: Lois M. Barber, 5128 E. Ocean Blvd., Long Beach, Calif. 90803

[22] Filed: Dec. 9, 1974

[21] Appl. No.: 530,819

[52] U.S. Cl. .............................. 128/77; 128/89 R
[51] Int. Cl.² .......................................... A61F 5/10
[58] Field of Search ............. 128/77, 87, 89, 90, 83

[56] References Cited
UNITED STATES PATENTS

| | | | |
|---|---|---|---|
| 2,312,523 | 3/1943 | Corbett | 128/87 A |
| 2,812,570 | 11/1957 | Petersilie et al. | 128/89 R |
| 2,958,325 | 11/1960 | Claydon et al. | 128/90 |
| 3,703,894 | 11/1972 | Galloway et al. | 128/77 |
| 3,776,225 | 12/1973 | Lonardo | 128/87 R |
| 3,788,307 | 1/1974 | Kistner | 128/87 R |
| 3,815,588 | 6/1974 | Kalusner | 128/77 |

FOREIGN PATENTS OR APPLICATIONS 574,529   1/1946   United Kingdom ............... 128/89 R Primary Examiner—John D. Yasko

[57] ABSTRACT

A lightweight, manually formable splint constructed of an underlying framework of aluminum wire alone or in conjunction with aluminum sheet, which is enclosed in polyethylene foam. The splint is especially designed for use in splinting hands.

9 Claims, 15 Drawing Figures

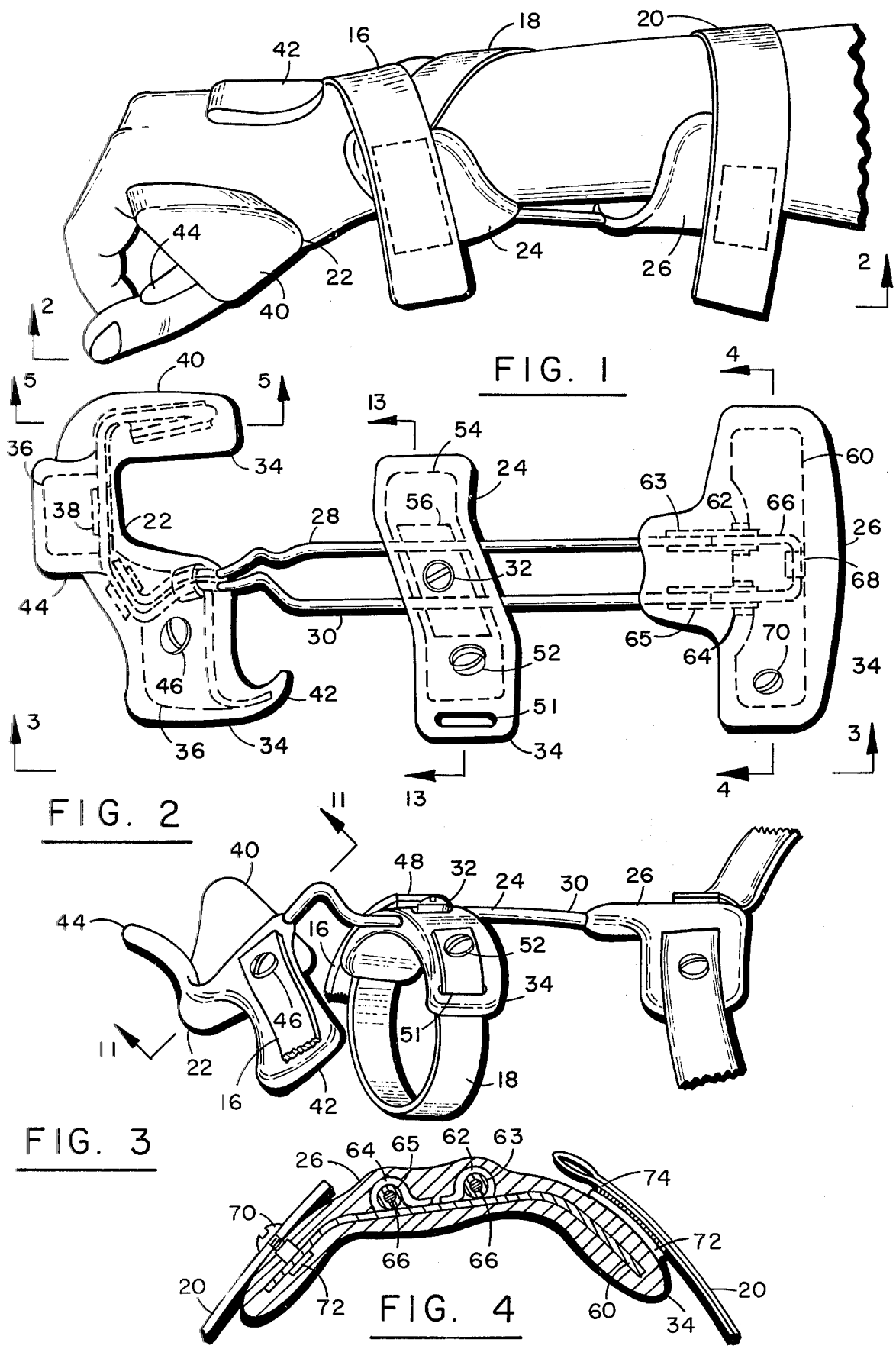

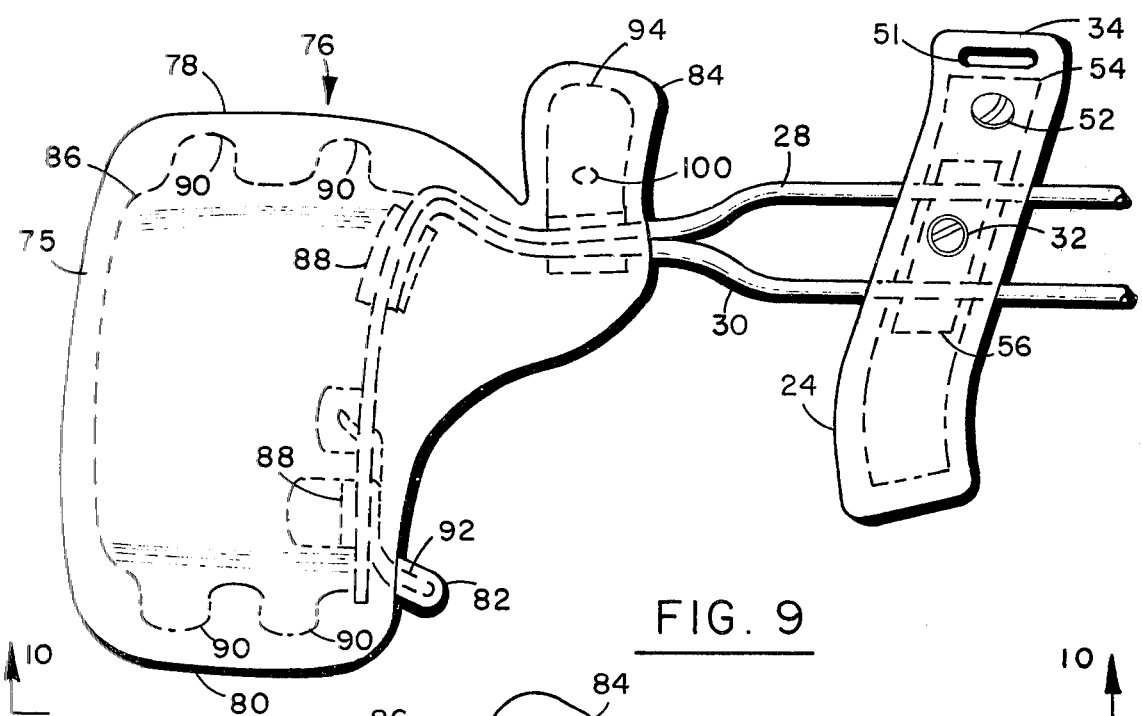
FIG. 9
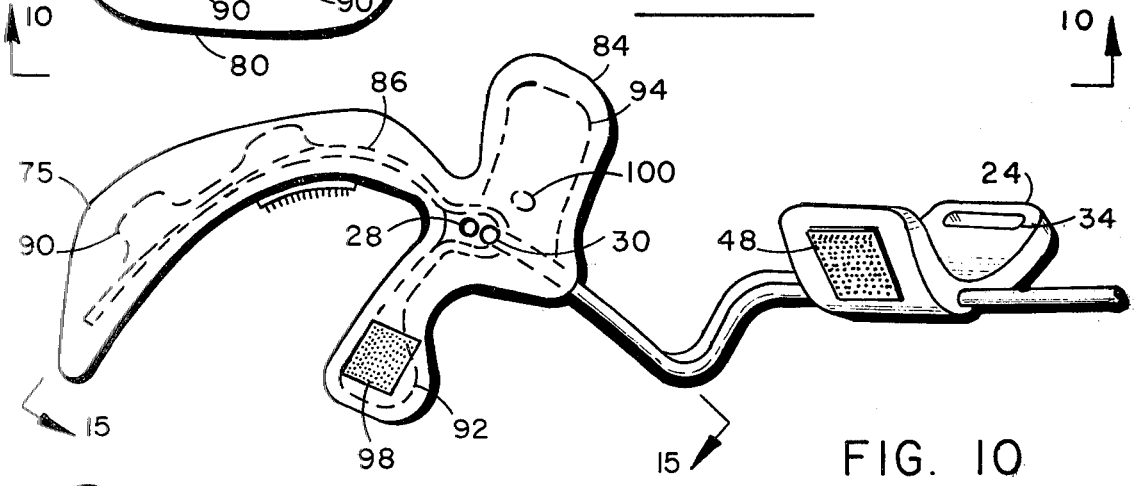
FIG. 10
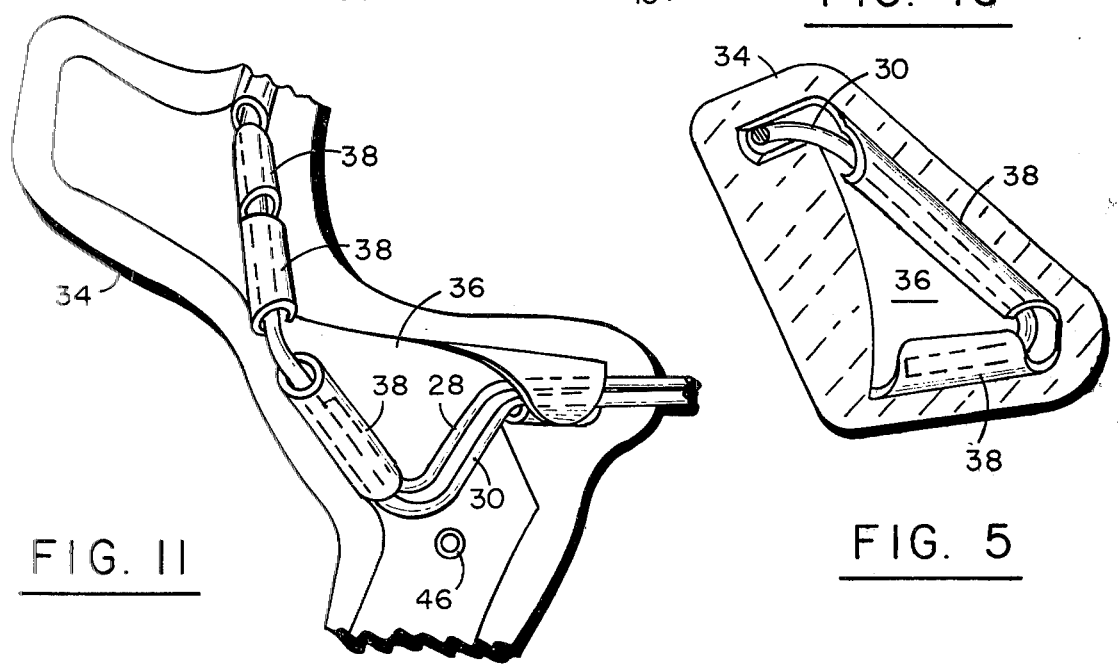
FIG. 11
FIG. 5

HAND SPLINT

BACKGROUND OF THE INVENTION

1. Field of the Invention

This invention relates to the field of splints and is particularly directed to a new hand splint as hereinafter described.

2. Description of the Prior Art

In the past, many types of materials have been used to form splints for the support of parts of the body.

Wood has long been used as a readily available lightweight splinting material in conjunction with bandages to hold the splint in place on the part of the body to be supported. While wood has the advantage of lightweight, low cost and availability, it suffers disadvantages of nonconformity to the part of the body to be supported. Also, its rigid nature does not allow for change in form.

In an attempt to overcome some of these deficiencies, other materials have been used in place of wood. These have included for example, metal in various forms, as well as castable materials such as plaster and plastics. The substitution of such materials did provide certain advantages, mainly consisting of conformity to the body part to be supported. However, they added other disadvantages.

For example, the use of metals, plasters and the like increased the weight of the splint which is highly undesirable. In addition, the hardness of these materials caused pressure points to develop and did not allow for any compensation for swelling. The result was added discomfort to the patient.

The casting materials required considerable time, not only in the casting procedure, but also in the setting time. Also, heat was often required, which was not usually well tolerated by the patient. The rigid nature did not allow for swelling or change requiring frequent replacement of casts. These were also subject to soiling and disintegration if wet, so that bathing remained an irritating problem. Other types of splints required special tools for the forming thereof, adding also to the time required for fitting.

In the splinting of arthritic patients, it is desirable that splints be easily formed to the user's hand and at the same time be capable of further adjustment. Also, it is desirable that such a splint be readily removable for readjustment as well as for patient comfort and to allow bathing.

From the standpoint of comfort, it has been found to be desirable that a splint be well ventilated, soft and strong, yet light in weight, and have long-lasting, non-rustable parts. Until the present time, there has been no such splint available which has embodied all of the above described advantages.

SUMMARY OF THE INVENTION

The novel hand splint of the invention combines the strength, lightweight, non-rusting and malleable characteristics of aluminum with the soft, flexible nature of polyethylene foam. The combination of an aluminum framework for the splint which is enclosed in polyethylene foam allows for the rapid fitting of the splint to a hand on an individual basis. The splint then conforms to the hand being supported and allows for further forming and change as required. All initial and subsequent adjustments of the splint can be made by hand bending of the splint.

The polyethylene foam provides a cushioning action to the hand, wrist and forearm at points of contact. Thus, pressure problems are avoided. Also, a sliding distal holding piece allows for conformity of the splint to a body member intermediately between the ends thereof. This feature is very important.

The splint itself can be washed as desired due to the tough, durable, waterproof material of which it is made. Additionally, the screw attachment of its straps makes them more removable for laundering.

The inclusion of a screw collar in the aluminum framework allow straps to be secured simply by forcing a hole in the soft cotton material of the strap, placing it over a screw collar and attaching the screw.

Velcro patches on the fill ends of the straps and adhered to the foam, allow for adjustments to compensate for swelling of the body parts as well as for easy attachment and removal thereof. This is of particular advantage to arthritic patients who find buckles and snaps difficult to handle. Furthermore, the open design of the splint provides good ventilation to the body parts, minimizing discomfort from perspiration.

In addition to the above advantages, the unique design of the splint takes into consideration the anatomical shape of the hand and arm to allow motion of the thumb and fingers when possible while providing support. By holding the hand in a fixed position, support is also provided to the wrist.

The splints of the invention have been found particularly useful in the treatment of arthritis, burns, infectious neuronitis, spinal cord injury, hemiplegia, peripheral nerve injury, brachial plexus injury, and traumatic head injury.

BRIEF DESCRIPTION OF THE DRAWINGS

The invention will be more clearly understood by reference to the description below taken in conjunction with the accompanying drawings wherein:

FIG. 1 shows a perspective view of a right hand splint according to the invention which is shown implaced on a user's arm;

FIG. 2 shows an underview of the splint alone with the straps removed as seen in the direction of lines 2—2 of FIG. 1; and details the major parts of the splint with the interior framework sketched in to show the construction thereof;

FIG. 3 shows another view of the splint of FIG. 1 as seen in the direction of lines 3—3 of FIG. 2;

FIG. 4 shows a cross section of the proximal holding piece of the splint of FIGS. 1 and 2 taken along lines 4—4 of FIG. 2;

FIG. 5 shows a cross section of part of the palm support piece of the splint of FIGS. 1 and 2 as shown in the direction of lines 5—5 of FIG. 2;

FIG. 6 shows a different embodiment of a right hand splint which has a framework made entirely of wire, and which shows the interior framework sketched in;

FIG. 9 shows a partially broken away view of a right hand splint which is substantially the same as the splint of FIGS. 1 and 2, with the exception that the palm support piece is different, and the underlying framework is shown sketched in;

FIG. 10 shows a side view of the splint of FIG. 9 as seen in the direction of lines 10—10 of FIG. 9, and with the support framework shown sketched in;

FIG. 11 shows a somewhat schematic cross section of the palm piece of FIGS. 1 through 3 as shown from the direction of lines 11—11 of FIG. 3;

DESCRIPTION OF THE PREFERRED EMBODIMENTS

Figure 6:
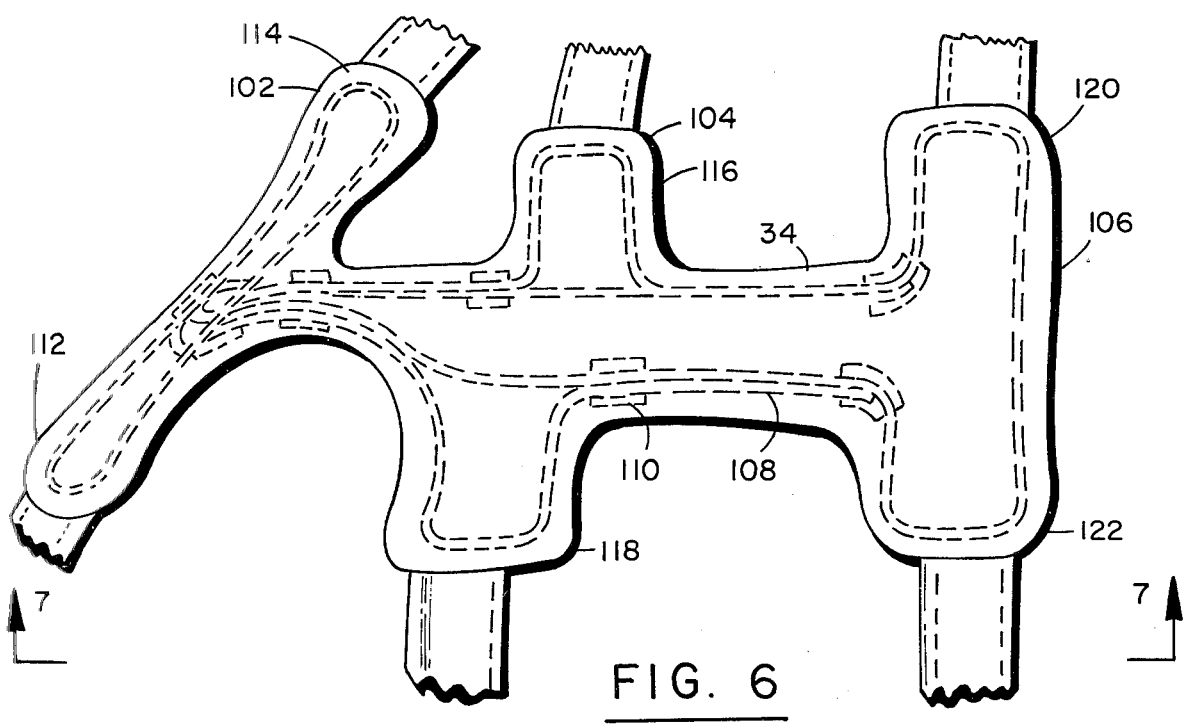

The drawings show three different embodiments of the wire foam splint of the invention. Each of these embodiments shows a right hand splint, each of which includes three major parts or pieces. Two of the embodiments have a framework of wire and metal sheeting, and a third embodiment has a framework entirely of wire. The preferred metal is aluminum due to its light weight, low cost and malleability. The drawings will be described with specific reference to use of aluminum. It should be understood however, that certain other metals can be used in place of aluminum.

Referring to FIG. 1 there is shown a perspective view of a splint according to the invention secured to a right hand and forearm by means of straps 16, 18 and 20.

As can be seen in greater detail in the underview of the splint shown in FIG. 2, the splint itself is formed of three major pieces: A palm piece 22 which supports the hand and thumb; a distal holding piece 24; and a proximal holding piece 26. Each of these pieces is joined together by means of two metal wires 28 and 30, preferably of aluminum. The distal piece 24 and the proximal piece 26 are secured to the forearms. The palm piece 22 is secured to the hand and held in position by means of the distal and proximal piece 24 and 26.

For purposes of better adjustment and fit, the wires 28 and 30 pass through the distal holding piece 24 which can be slid along the wires 28 and 30. When the distal piece 24 has been placed in the desired position on wires 28 and 30, it is anchored in place by means of tightening a screw 32.

The wires 28 and 30 which run parallel to the longitudinal axis of the arm give strength to the splint and permit sliding the distal piece for individual fit. Before the wires 28 and 30 come together at the palm piece 22, they are bent at an angle to increase strength and avoid wrist contact which could cause pressure points.

Each of the pieces includes an underlying framework of metal, preferably aluminum sheeting, portions of which are crimped around the wires 28 and 30 to secure them thereto.

A plastic foam material 34, which is preferably a polyethylene foam, encloses each of the splint portions 22, 24 and 26. The plastic foam 34 provides a cushioning effect to the splint and should be flexible to provide forming of the splint pieces by bending of the framework without separation of the plastic foam from the splint.

While the preferred foam 34 is a polyethylene foam, other types of foam can be used. Examples include, but are not limited to, polypropylene foam, ionomer foam, polystyrene foam, polyurethane foam, PVC (Polyvinylchloride) flexible foam, and silicone foam. The above examples are not intended to be limiting, but only exemplative of the types of materials which can be used. Some of the above mentioned foams may require an adhesive to improve bonding of the foam layers together.

The advantages of the use of polyethylene foam include the characteristics of low water absorption, good energy absorption, water vapor barrier, compressability, smooth surface, temperature resistance of 100° to 180° F., and a high ratio of tensile and shear strength to weight compared to other resilient foams. Furthermore, polyethylene foam is particularly desirable for use in the wire splint because it can be bonded to itself without any additional adhesive.

As shown in FIG. 2, the underlying framework of the major pieces 22, 24 and 26 of the splint is sketched in. As above stated, each of these includes a metal sheet material, preferably aluminum, which is secured to the wires 28 and 30, and then enclosed in foam 34.

Beginning with the palm support piece 22 of FIG. 2, it can be seen that the wires 28 and 30 are bent to provide support to the palm piece 22. In addition to the wires 18 and 20 in the palm piece 22, there is also a piece of aluminum sheet 36 which can be seen in greater detail in FIGS. 5 and 11. The aluminum sheet 36 is secured to the wires 28 and 30 by means of crimping over portions of the aluminum sheet 36. These crimped over portions are indicated at 38 in FIGS. 5 and 11.

Surrounding the aluminum sheet and aluminum wire support framework in a sandwich arrangement, is the foam 34. In FIG. 11, the foam in the top section has been removed to better show the underlying wire within the sheet framework.

The palm support piece 22 is designed to conform to the anatomical structure of the hand. Thus, the palm piece 22 is designed to lie proximally to the distal palmar crease. This allows for full motion of the fingers through the metacarpophalangeal joints. In addition, the palm support piece 22 is bent to accommodate the curve of the palmer arch. The palm support piece 22 includes an upwardly extending wing 42, a lateral wing 40, and a downwardly extending thumb abduction piece 44.

As can be seen, with the hand in place in the splint in FIG. 1, the wing 42 provides support to the metacarpal bones of the ulnar side of the hand. At the same time, the lateral wing 40 provides support to the metacarpal bone of the thumb. The thumb rests on and is held in place in an abducted position by means of the thumb abduction wing 44.

The design of the splint in FIG. 1 allows for free motion of the fingers and limited use of the thumb. Also, the relatively wide supportive surface avoids pressure points by distributing pressure over a wide area, contributing considerably to the comfort of the splint.

The palm support piece 22 also includes a screw 46 for purposes of anchoring a strap thereto. As shown in FIG. 1, a strap which has been doubled over itself to form straps 16 and 18 is secured at the doubled over portion to the underside of the distal holding piece 24. This is made possible by means of velcro strips 48 and 50 secured to the strap and to the foam padding respectively.

The strap 16 as shown, passes over the back of the hand and wrist to wrap around the carpal bones of the wrist. It is secured to the underside of the wing 42 of palm piece 22 by means of the screw 46 as shown in FIG. 2. The strap 18 wraps around the back of the forearm and passes through slot 51 to hold it in place and is secured to the distal piece 24 by means of the screw 52.

After the splint has been properly fitted, the velcro strips 48 and 50 allow for the easy one hand securement and removal of the splint whenever desired. The use of the double strap as above described takes advantage of the protruding portion of the ulnar bone to hold the straps in place and avoid slippage thereof.

As mentioned previously, the distal portion 24 of the splint helps to hold the splint in place by providing radial and ulnar contact to the forearm. It is angularly oriented to the longitudinal axis of the arm and to the wires 28 and 30. That is, the radial contact of the distal piece is closer to the hand than the ulnar contact. This angular placement is designed to keep the palmar support 22 from slipping distally.

The underlying framework of the distal piece 24 of the splint is shown sketched in, in FIG. 2. The support framework includes an aluminum sheet 54 and a smaller stainless steel plate 56. The wires 28 and 30 are sandwiched between and clamped by aluminum sheet 54 and stainless steel plate 56.

Figure 13:
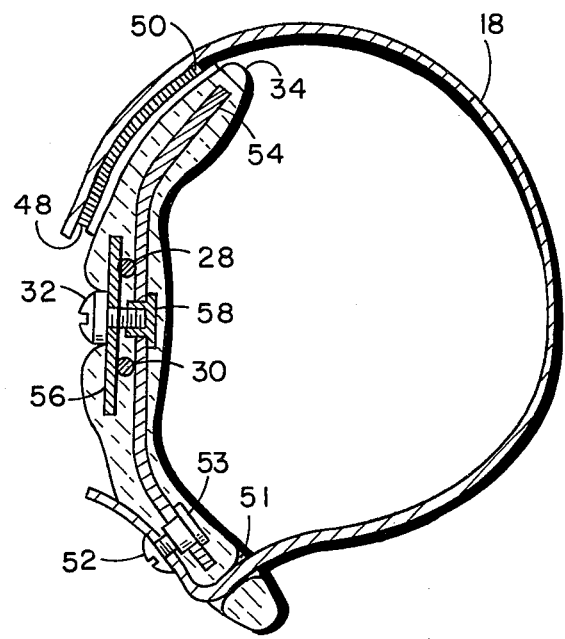
FIG. 13 shows a cross section of the distal holding piece of the splint of FIG. 2 as taken in the direction of line 13 of FIG. 2.

The arrangement of the plate 56 and aluminum sheet 54 on either side of the wires 28 and 30, allow for sliding in either direction of the entire distal holding piece 24 along the wires 28 and 30. When the desired position has been reached, it can be held tightly in place by tightening screw 32 which passes through an unthreaded collar 33, foam 34, plate 56, and is anchored in the aluminum sheet 54 by means of a threaded collar 58. This arrangement can be seen in detail in the cross section of FIG. 13.

The proximal piece 26 which aids in positioning the splint on the forearm is shown in FIGS. 1, 2, 3 and in cross section in FIG. 4. The proximal piece 26 includes an underlying framework of aluminum sheet 60, portions of which 62 and 64 are crimped over tubes 63 and 65 which enclose the ends of wires 28 and 30. The ends of a U-shaped piece of wire 66 are fitted into the tubes 63 and 65 to meet wires 28 and 30 as shown. The U-shaped piece 66 is also held in place by means of the crimping over of portion 68 of the sheet 60.

A screw 70 of the type used in the palm piece and the proximal piece passes through sheet 60 for purposes of securing strap 20 thereto. The screw 70 is anchored by means of a threaded collar 72 as shown in FIG. 4. A pair of velcro patches 74 and 76 on the back of the proximal piece 26 are secured to the foam 34 and to the strap 20 respectively to allow for the easy attachment and removal of the strap 20. This can be seen in the cross section of FIG. 4.

Figure 15:
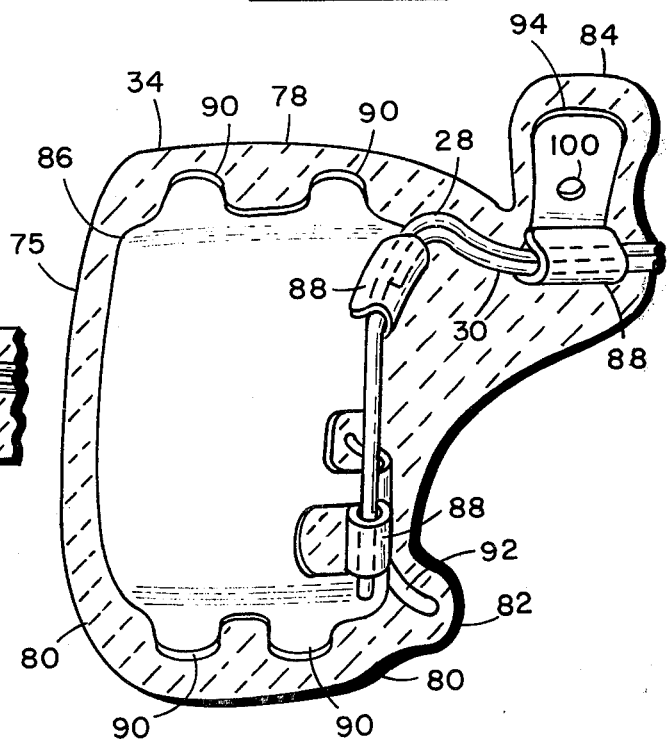

The hand splint embodiment which is shown in FIGS. 9, 10 and 15 is essentially the same as that shown in FIGS. 1 through 3, with the exception that the palm support piece is different. The distal piece and the proximal piece are exactly the same. In FIGS. 9 and 10 the proximal piece is not shown in the drawing. Only the distal piece is shown. For purposes of clarity, the same numbering will be used for this support piece.

As shown in FIG. 9, the palm support piece has a major curved support area or platform 75 which generally conforms to the length and width of the hand. The platform 75 can be adjusted by bending it to the desired degree of flexion of the metacarpophalangeal and interphalangeal joints. On the sides, the platform 75 extends upwardly into wings 78 and 80. The wings cup the fingers and hold them in alignment avoiding deviation of the fingers. Beneath the curved platform 75 is a thumb abduction wing 82. An upwardly extending wing 84 provides support to the ulnar side of the hand.

The underlying aluminum sheet and wire framework is shown sketched in FIG. 9 allows for bending at the line of the metacarpophalangeal and interphalangeal joints. As shown in FIG. 9 and detailed in FIG. 15, the framework of the splint includes aluminum wires 28 and 30 which are secured to an aluminum sheet 86 by means of crimped over areas 88 as shown.

The aluminum sheet 86 projects into the lateral wings 78 and 80 by means of projections 90; into the thumb abduction wing by means of projection 92; and into the lateral wing by means of projection 94. This arrangement can be seen by reference to FIG. 15 which shows the upper layer of polyethylene foam removed to more clearly show the underlying aluminum sheet and wire framework.

The splint of FIGS. 9 and 10 is provided with a velcro patch 96 on the underside of the finger platform. Another velcro patch 98 is provided on the underside of the thumb abduction wing 82. These velcro patches are used in conjunction with betapile straps which adhere to the velcro patches. The straps are used to hold the fingers on the platform 75 and to hold the thumb in place against the thumb abduction support wing 82.

The remaining strapping of the splint is the same as that described for the embodiment of FIG. 1. Thus, a pair of straps formed from a single folded strap as described for distal holding piece 24 of FIGS. 1 and 2 is secured to a velcro strip 48 at the point where it is folded over. One of the straps is then passed over the back of the arm and threaded through slot 51 of distal holding piece 24 and secured by means of screw 52. The other strap is secured to the palm support piece 76 by means of a screw 100 in the lateral wing 84. The screw lies on the underside of the wing 84 and therefore has been shown only as being sketched in. It is secured in the framework by screwing into a threaded collar, not shown.

It should be mentioned here that in the two embodiments which have been described, that it has been found to be advantageous to tape any sharp areas in the aluminum framework with aluminum duct tape or equivalent, in order to prevent the possibility of the frame from wearing through the foam plastic exterior.

In the final embodiment, which is shown in FIGS. 6, 7, 8, 12 and 14, the splint has an underlying framework which is made up entirely of aluminum wire. The splint is similar to the above described embodiment in that it is comprised of three major parts or pieces: the palm support piece 102; the distal holding piece 104; and the proximal holding piece 106. Similarly, the palm support piece 102 has been designed to lie proximally to the distal palmar crease. The result is that full use of the fingers is possible when using the splint. Additionally, the distal holding piece 104 is angularly oriented to the longitudinal axis of the arm in order to prevent support 102 from slipping distally.

As shown in FIG. 6, the underlying support framework has been sketched in. It can be seen that it is formed entirely of a wire 108 with taped areas 110. These have been provided not only to cover up any sharp areas, but also to provide additional strength to the splint by holding together the wires as shown. As can be seen, the wire extends in a peripheral manner throughout the palm support piece 102, the distal holding piece 104, and the proximal holding piece 106.

Figure 12:
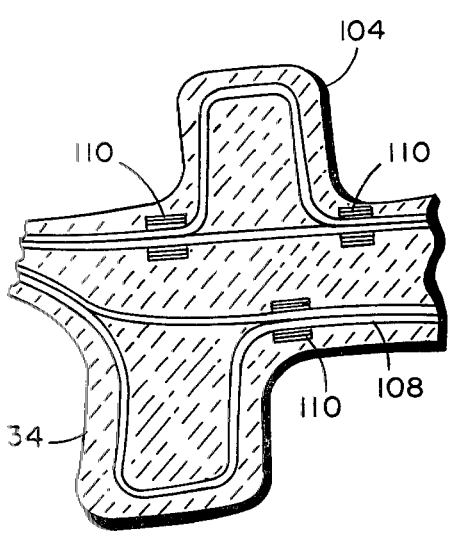
FIG. 12 shows an enlarged detailed view of the proximal holding piece of the splint of FIG. 6 with the top foam layer removed, as shown in the direction of lines 12—12 of FIG. 8.
Figure 14:
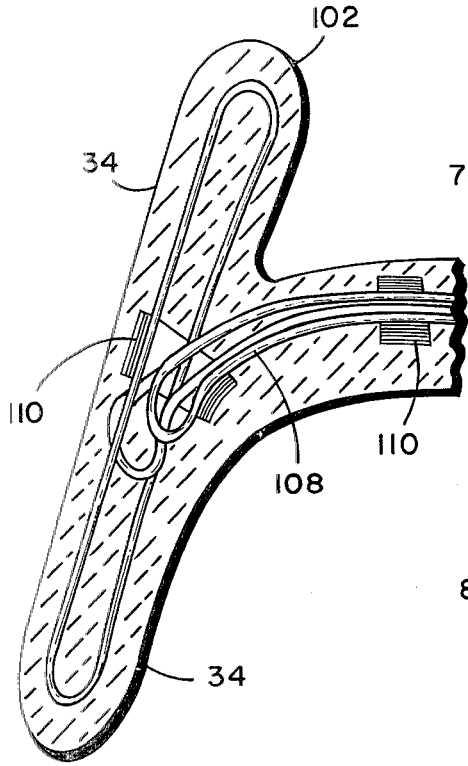
FIG. 14 shows an enlarged detailed view of the palm support piece of the splint of FIGS. 6 and 7 with the top foam layer removed, as shown generally in the direction of lines 14—14 of FIG. 7; and, FIG. 15 shows a somewhat schematic plan view of the palm support piece of the splint of FIGS. 9 and 10 as shown from the direction of lines 15—15 of FIG. 10, with the top foam layer removed to reveal the underlying framework.

This underlying framework composed of the wire 108 and tapes 110 is particularly detailed in FIG. 12 showing the distal holding piece 104 and in FIG. 14 showing the palm support piece 102.

Figure 7:
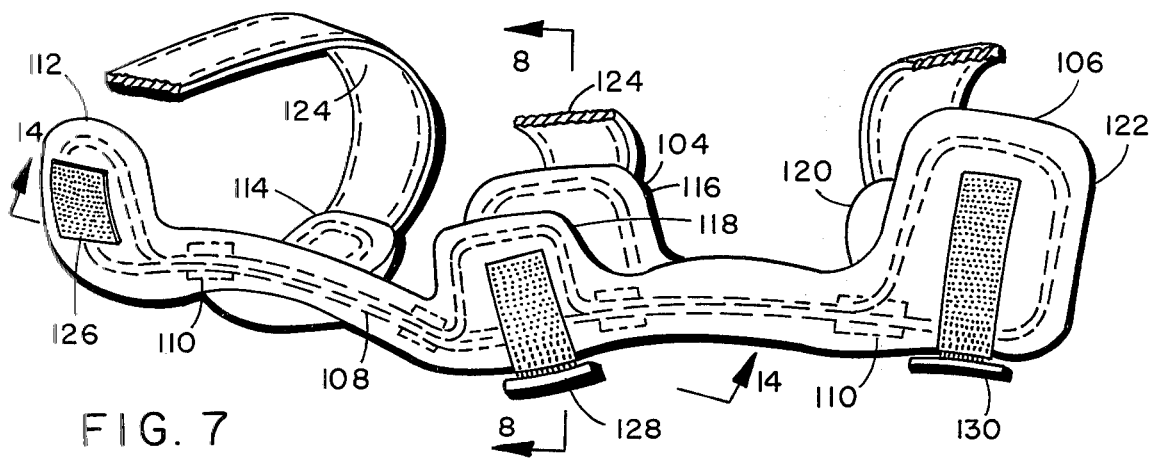
FIG. 7 shows a side view of the splint of FIG. 6 as shown in the direction of lines 7—7 of FIG. 6.
Figure 8:
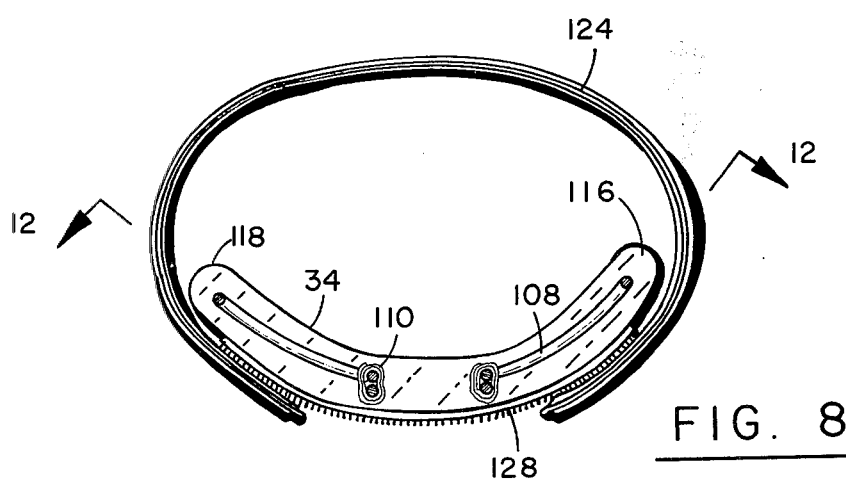
FIG. 8 shows a cross section of the distal holding piece of the splint of FIGS. 6 and 7 as seen from the direction 8—8 of FIG. 7.

As can be seen in FIGS. 6 and 7, the palm support piece 102 of the splint is bent to provide support to the palmar arch. The ends are bent upwardly into two wings 112 and 114 to provide support to the metacarpal bones of the index and little fingers of the hand. By this design, free movement of the thumb and fingers are possible while at the same time the hand is being supported.

The use of the wire makes this splint extremely light in weight and more malleable than the first two embodiments described.

The distal holding piece 104 is also bent into upwardly extending wings 116 and 118 aiding securement to the wrist and forearm. Similarly, the proximal holding area is bent up to form wings 120 and 122.

On the underside of the support wings of the palm 102, distal 104 and proximal 106 pieces are velcro patches. These are used in conjunction with betapile straps 124 which by their nature adhere to velcro patches. In FIG. 7, velcro patch 126 can be seen under wing 112 of palm piece 102. In the distal holding piece 104, as well as under the proximal holding piece 106, a velcro patch runs substantially under the entire support area. Thus, as shown in FIG. 7, velcro patch 128 extends under distal holding piece 104, and velcro patch 130 extends under proximal holding piece 106. This can be seen with greater clarity in FIG. 8.

Betapile straps provide a very soft, lightweight securement means which is capable of easy adjustment as well as attachment around the hand and arm.

It will be apparent that other fastening means can be used in place of the velcro pile straps, or velcro patches sewn to cotton straps as shown in the drawings. For example, buckles, snaps, buttons, hooks, and the like can be employed. However, these are not as preferred, since they do not provide the easy adjustment which is obtainable through the use of velcro patches.

Aluminum is most preferred as the framework metal because of its light weight in combination with the above mentioned advantages. Also, it is low in cost relative to other metals at this time. However, other lightweight reinforcing metals could be used in place of aluminum. Such metals should provide the strength and malleable characteristics of aluminum. Examples of such metals would include among others, copper, steel, brass and the like.

The wire splints shown in the drawings are for a right hand splint. Left hand splints would be the mirror image of the right hand splint.

Various modifications can be resorted to without departing from the spirit and scope of the invention as defined by the following dependent claims.

I claim:

1. A hand splint comprising:
a manually bendable support medium formed of a framework of metal, and having a pliant cushioning material enclosing at least the major portions of said framework;
said splint including as major pieces,
a palm piece, a distal piece and a proximal piece;
said palm, distal and proximal pieces being substantially arcuate in shape; and wherein,
said palm piece includes a palm support portion which is adapted to lie proximally to the distal palmar crease; and wherein;
said distal piece is angularly oriented relative to the longitudinal axis of an arm, is adapted to provide radial and ulnar contact, the radial contact being closer to the hand than the ulnar contact;
at least one longitudinally oriented connecting wires joining said major splint pieces; and,
straps attached to said hand splint to secure it to a hand and forearm.

2. A splint as claimed in claim 1 wherein:
said framework support medium is formed entirely of a metal wire bent over on itself to provide two wire support in each of the major splint pieces; and,
at least two wire support in the longitudinal connecting portions of the splint.

3. A splint as claimed in claim 2 wherein:
said two-wire support in said major splint pieces is substantially peripheral to said major splint pieces and is of aluminum; and wherein,
said cushioning material is polyethylene foam.

4. A wire splint as claimed in claim 1 wherein:
each of said major splint pieces is connected by a two-wire support, said wire support being spaced apart through said distal and proximal splint pieces;
said proximal piece framework is formed of a piece of sheet metal bent to provide the support, a portion of which is secured to said wire support;
said distal splint piece being angularly oriented to the longitudinal axis of the splint providing radial and ulnar contact, the radial contact being closer to the hand than the ulnar contact, and including as the framework a pair of metal sheets between which the wire supports pass, one of said sheets being larger and acting as the supporting framework, the other being smaller and cooperating with said first sheet to clamp said wires;
locking means on said metal sheets to permit sliding of said sheets along said wire supports and subsequent securement thereto; and,
said hand support piece being formed of a bent metal sheet secured to said wire supports.

5. A splint as claimed in claim 4 wherein:
said wire and sheets are formed of aluminum,
said foam is polyethylene foam; and,
said securing means comprises velcro patches secured to said foam and to said straps.

6. A splint as claimed in claim 5 wherein:
one end of said straps is secured to a velcro patch on the underside of the support pieces while the other end of the straps is secured to the underside of said support pieces by means of a threaded collar and screw, the threaded collar of which passes through the foam cover of the underside of the splint and is secured to the underlying plate.

7. A splint as claimed in claim 6 wherein:
said securement means further comprises:

a folded over strap secured at the fold to the radial side of said distal splint piece, a slot and a securing screw on the ulnar side of said distal splint piece, one of said straps passing through the slot and secured by the screw, the remaining strap passing over the back of the wrist and secured to the palm support piece by means of a securing screw on the underside thereof.

8. A splint as claimed in claim 5 wherein:

the framework of said palm support piece is formed of a bent piece of aluminum sheet having an upwardly extending wing to support the ulnar side of the hand, a transverse section being proximal to the distal palmar crease, with a downwardly extending thumb abduction wing, and a lateral wing extending along the thumb metacarpal toward the body to hold the thumb in an abducted position; and, said aluminum sheets of said palm and proximal splint pieces being secured to said aluminum wire by means of crimped over parts of said sheets around said wires.

9. A splint as claimed in claim 5 wherein:

the framework of said palm support piece is formed of a bent piece of aluminum sheet having an upwardly extending wing to support the ulnar side of the hand, a transverse section in the form of a curved platform for the fingers and extending upwardly along the sides of the index and little fingers, and a downwardly extending thumb abduction wing; and said aluminum sheets of said palm and proximal pieces being secured to said aluminum wire by means of crimped over parts of said sheets around said wires.

\* \* \* \* \*